United States Patent [19]

Norman et al.

[11] Patent Number: 5,319,118
[45] Date of Patent: Jun. 7, 1994

[54] VOLATILE BARIUM PRECURSOR AND USE OF PRECURSOR IN OMCVD PROCESS

[75] Inventors: John A. T. Norman, Enciritas, Calif.; Beth A. Muratore, Elverson, Pa.; Paul N. Dyer, Allentown, Pa.

[73] Assignee: Air Products and Chemicals, Inc., Allentown, Pa.

[21] Appl. No.: 779,435

[22] Filed: Oct. 17, 1991

[51] Int. Cl.$^5$ .............................................. C07F 3/00
[52] U.S. Cl. ........................................ 556/2; 568/382
[58] Field of Search ............................. 556/2; 568/382

[56] References Cited

U.S. PATENT DOCUMENTS 4,501,602  2/1985  Miller et al. ......................... 65/18.2
4,558,144  12/1985  Fay et al. ................................ 556/40

FOREIGN PATENT DOCUMENTS 0405634  2/1991  European Pat. Off. .

OTHER PUBLICATIONS

K. Shinohara, et al., "Preparation of Y–Ba–Cu–O Superconducting Thin Film by Chemical Vapor Deposition" Jap. J. Appl. Physics, vol. 27, No. 9, Sep. 1988, pp. L1683–L1685.

S. Oda, et al., "Epoitoxial Growth of Y–Ba–CuO Films on Sapphire at 500° C. by Metalorganic Chemical Vapor Deposition," Jap. J. Appl. Physics, vol. 28, No. 3, Mar. 1989, pp. L427–L429.

R. E. Sievers, et al., "Volatile Metal Complexes", Science, vol. 201, 21 Jul. 1978, No. 4352, p. 217.

A. P. Purdy, et al., "Chemical Vapor Deposition Experiments Using New Fluorinated Acetylacionates of Calcium, Strontium, and Barium," Inorg Chem., 1989, vol. 28, pp. 2799–2803.

Y. Hisonori, et al., "High Critical–current density of Y–Ba–Cu–O superconducting films prepared by CVD," Supercond. Sci. Tech., vol. 2 (1989) pp. 115–117.

A. J. Panson, et al., "Chemical Vapor depositon of $YBa_2Cu_3O_9$ using metalorganic chelate precursors," Appl. Phys. Lett., vol. 5, No. 18 pp. 1756–1768 (1988).

M. J. McCormick, et al. "Synthesis for Monopentamethylcyclopentadienyl Halide Complex of Calcium The X-Ray Crystal Structure of $[(Me_5–_5)-Ca(u–I)(THF)_2]_2$", Organmetallis, vol. 8 No. 8 pp. 2044–2049 (1989).

T. Dakamori, et al., "Superconducting of Y–Ba–Cu–O Oxide Films by OMCVD", Jap. J. Appl. Physics, vol. 27, No. 7, Jul., 1988, pp. L1265–L1267.

J. Zhau, et al., "Organometallic Chemical Vapor Deposition of High $T_c$ superconducting films using a violatile, fluorocarbon–based precurosr", Appl. Phys. Lett. 53 (18), Oct. 31, 1988, pp. 1750–1752.

A. D. Berry, et al., "OMCVD of thin films from metal-dipitonates and triphenylvismuth", J. Mater. Res., vol. 5, No. 6 (Jun. 1990) p. 1169.

P. H. Dickinson, et al., "Chemical vapor depositon of $Ba_2Cu_3O_{7-x}$ superconducting films", J. Appl. Phys. vol. 66, p. 444 (1989).

A. R. Barron, "Group 11A Metal–Organics as MOCVD–Precursor for High $T_c$ Superconductors", MRS Symp. Proc. Fall Meeting Boston, Nov. 1990.

F. Schnaderer, et al., "High $T_c YBa_2Cu_2O_{7-8}$) prepared by chemical vapour deposition", Appl. Surface Science, vol. 46, (1990) pp. 53–60.

S. Matsuono, "Y–Ba–Cu–O Superconducting Films with High-$T_c$ Values by MOCVD using Ba–Addition Products," Jap. J. Appl. Physics, vol. 29, No. 6, Jun. 1990, pp. L949–L948.

C. S. Chern eta l., "Insity growth of $YBa_2Cu_3O_{7-x}$ high $T_c$ superconducting thin films directly in sapphire by (List continued on next page.)

Primary Examiner—José G. Dees
Assistant Examiner—Porfirio Nazario
Attorney, Agent, or Firm—Mark L. Rodgers; William F. Marsh

[57] ABSTRACT

Novel volatile barium complexes are disclosed which are very stable and evaporate cleanly at elevated temperatures. Such complexes are highly suited for use as a barium source in OMCVD processes.

3 Claims, 8 Drawing Sheets

OTHER PUBLICATIONS plasma-enhanced matallorganic chemical vapor deposition", Appl. Pys. Lett., 59, (7), Aug. 13, 1990, p. 721.

Ed. by K. K. Schurgraf, (Ronald C. Rossi), "Handbook of Thin Film Deposition Processes Techniques" Noyes Publication, 1988, Chapter 3.

A. Glizes, "Crystalline structure of bis(2,2,6,6-tetramethl-3,5-heptanedionates) barium", C. R. Acad. Sci. Paris, vol. 312, II pp. 983-988 (Mar. 1991).

S. B. Turnipseed, et al. "Synthesis and characterization of Alkaline-Earth-Metal B-Depintate Complexes Used as Precursors in Chemical Vapor Depositon of Thin-Film Superconductors", Inorganic Chem. in Paris (1991).

◐ = BARIUM
◉ = OXYGEN
○ = CARBON

◐ = BARIUM
◉ = OXYGEN
○ = CARBON

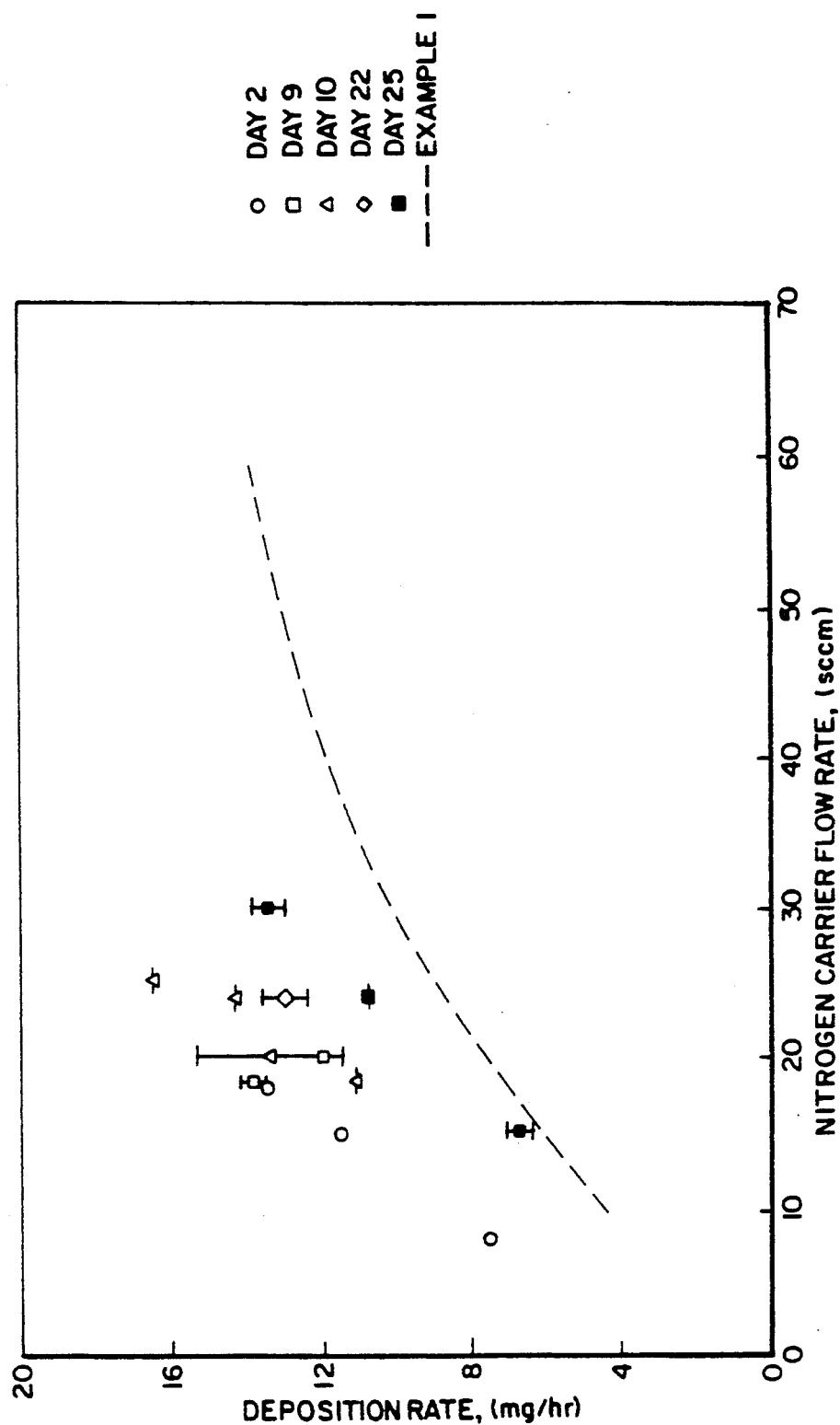

VOLATILE BARIUM PRECURSOR AND USE OF PRECURSOR IN OMCVD PROCESS

FIELD OF THE INVENTION

This invention relates to volatile barium complexes that are useful in organometallic chemical vapor deposition (OMCVD) processes.

BACKGROUND OF THE INVENTION

There is a growing economic need for precursors, having applications in OMCVD processes to fabricate alkaline earth metal (i.e. barium, strontium and the like) containing materials, that are cleanly volatile sources for such metals. To be useful, such a precursor must be able to deliver a steady gas phase transport of metal-containing vapor during the CVD process to deposit a thin film of the metal or metal-containing compound onto a substrate. It is especially important that the vapor pressure of the metal precursor is stable over time to permit precise control over the elemental composition in the final product.

Examples of alkaline earth containing materials produced in a CVD process are high temperature superconducting (HTSC) ceramic thin films being developed for use in microelectronic devices. In a typical high temperature superconductor (HTSC) thin film CVD process, a vapor containing "volatile" organometallic compounds of barium, yttrium and copper, e.g. bis(1,1,1,5,5,5-hexafluoro-2,4-pentanedionato) barium-(II) [$Ba(HFA)_2$], tris(2,2,6,6-tetramethyl-3,5-heptanedionato)yttrium(III) [$Y(DPM)_3$], and bis(1,1,1,5,5,5-hexafluoro-2,4-pentanedionato)copper(II) [$Cu(HFA)_2$], is contacted with oxygen over a $SrTiO_3$ substrate at 10 Torr pressure and a temperature of 600° C. to deposit an amorphous thin film. After further annealing in air for three hours at 850° C., a high temperature superconducting ceramic thin film is produced with the composition $YBa_2Cu_3O_y$; see K. Shinohara et al Japanese Journal Appl. Phy., Vol. 27, No. 9, pp. L1683–L1685 (1988) and S. Oda et al, Japanese Journal Appl. Phy., Part 2, Vol. 28, No. 3, pp. L427–L429 (1989). The use of the fluorinated barium precursor results in the initial formation of $BaF_2$ which has to be subsequently annealed with water vapor and/or air to produce the desired oxide phase. To produce directly high quality single crystal or epitaxial mixed oxide films, it is important to avoid the initial formation of $BaF_2$ to enable the growth of the mixed Y-Ba-Cu oxides. It is therefore desirable to have a precursor that is non-fluorinated for CVD fabrication of HTSC mixed oxide thin films or other barium oxide-based films containing no fluoride. As previously stated, it is also desirable to have a precursor that is cleanly volatile, i.e. volatilizes without decomposition of the source, for accurate control over extended time periods of the stoichiometry of the CVD deposited barium oxide containing thin film.

The two most commonly utilized strategies for preparing volatile barium precursors are the use of bulky or fluorinated ligands that effectively screen barium ions from each other within the molecular structure of the complexes. This is thought to reduce intermolecular associations between barium centers and hence increase their volatility or at least reduce the intermolecular associations to the point where some vaporization is possible. This general phenomenon has been widely exploited in the preparation of volatile metal complexes in general; see R. E. Sievers, Science, Vol. 201, No. 4352, pp. 217–223, (1978). Due to its large ionic radius and propensity towards large coordination spheres, barium is a particularly difficult element to totally screen in this way and "molecularly encapsulate" to yield monomeric compounds. Bulky ligands such as bis(2,2,6,6-tetramethyl-3,5-heptanedionato) barium (II) (thd) and similar $\beta$-diketonates (including fluorinated $\beta$-diketonates) are limited in their ability to completely supply the degree of coordinate saturation required to achieve monomeric barium complexes. However, even though this deficiency can lead to complexes that are unstable towards sublimation (see A. P. Purdy et al, Inorg. Chem., Vol. 28, pp. 2799–2803 (1989)) there are reports of using bulky and fluorinated $\beta$-diketonate barium complexes and "$Ba(thd)_2$" in CVD processes; see Y. Hianori et al, Supercond. Sci. Technology Vol. 2, pp. 115–117 (1989) and A. J. Panson et al, Appl. Phys. Lett., Vol. 53, No. 18, pp. 1756–8 (1988). Similarly, there are other barium complexes that contain simple ligands (i.e. methyl or ethyl groups) that are also unable to supply the degree of shielding required to yield monomeric complexes; see M. J. McCormick et al., Organometallics, Vol. 8, No. 8, pp. 2044–2049 (1989). This can lead to polymeric or highly associated and hence sometimes involatile compounds of the type $(Ba^{+2})_x(L^-)_y$ where $y = 2x$. With $y = 2-10$, volatile character can be expected but when $y > 10$ polymeric involatile compounds result. Under conditions of strong heating the structure of these polymeric species may break down and in the process release molecular fragments that are more volatile. However this kind of "volatility" is uncontrolled and yields a vapor of constantly changing chemical composition which is unsuited to CVD processes.

Currently, the non-fluorinated barium precursor most widely used for CVD purposes is bis(2,2,6,6-tetramethyl-3,5-heptanedionato) barium(II), more commonly known and incorrectly formulated (vide infra) as "$Ba(thd)_2$" or "$Ba(tmhd)_2$" or "$Ba(DPM)_2$". However, notwithstanding the popular use of this material as a volatile precursor, it is known to be thermally unstable at CVD source delivery temperatures and to not be cleanly volatile, i.e. the composition of the vaporized material and its vapor pressure vary as a function of time. This causes difficulties in the control of the composition of the deposited film, and therefore in obtaining the desired physical and chemical properties.

It has been concluded there are problems in the OMCVD deposition of $YBa_2Cu_3O_y$ caused by the high vaporization temperature of "$Ba(thd)_2$" precursor and its limited thermal stability; see T. Nakamori et al, Japanese J. Appl. Phys., Vol 27, pp. L1265–L1267 (1988). The authors point out a solution to the problem would be an organic metal chelate having a lower vaporization temperature and a higher thermal stability. The performance of $Ba(dipivaloylmethanate)_2$, "$Ba(DPM)_2$" or "$Ba(thd)_2$", for OMCVD has been criticized for its low volatility, substantial decomposition during transport, lack of vapor pressure reproducibility and low deposition rates; J. Zhao et al, Amer. Appl. Phys. Lett., Vol 53, No. 18, pp.1750–1752, (1988). It has been observed qualitatively that barium diketonates, such as "$Ba(thd)_2$", are hygroscopic, with coordinated water removed under mild conditions prior to their use as OMCVD precursors, and that there is a need to avoid exposure to moisture following anhydrous synthesis;

see A. D. Berry et al, J. Mater. Res., Vol. 5, No. 6 (June, 1990).

One technique for improving the volatility of barium compounds that do not cleanly sublime without decomposition is to add small neutral molecules to the metal centers of these compounds to form volatile adducts. This helps to prevent ligands being shared between metal centers and hence promotes monomeric nature and volatility. Examples of this approach include the use of tetrahydrofuran (THF) and 1,2-dimethoxyethane (diglyme) to increase the volatility of both magnesium and zinc β-diketonates; S. B. Miller et al., U.S. Pat. No. 4,501,602 and R. C. Fay et al, U.S. Pat. No. 4,558,144.

Recently TNO (a division of Technology for Society. Dept Chemistry, P.O. Box 108, 3700 A. C. Zeist, Utrechtseweg 48, Zeist, The Netherlands) disclosed in EPO Patent Application 90201485.1 the preparation of volatile derivatives of barium β-diketonates by treating parent complexes with various linear polyether glymes such as tetraglyme. A problem with this kind of approach is that under heating conditions the added ligands tend to dissociate from the parent complex thereby precluding vaporization of the adduct.

Excess ligand can be added in the form of a saturated carrier gas to suppress dissociation of the adduct and this has been shown to be effective for "Ba(thd)$_2$" when adding either excess the ligand (P. H. Dickinsen et al, J. Appl. Phys., Vol. 66, pp. 444 (1989)) or excess simple amine; see A. Barron, MRS Symp. Proc., Fall Meeting, Boston, November 1990.

According to the above P. H. Dickerson et al reference, the partial thermal decomposition of "Ba(thd)$_2$" during transport may be avoided by using an inert carrier gas pre-saturated with organometallic ligand H(thd), which achieves stable precursor vaporization over a period of "several hours".

The stable delivery of "Ba(thd)$_2$" has been achieved over a period of 80 minutes using a carrier gas enriched with H(thd) as proposed by F. Schmaderer et al., Applied Surface Science, Vol. 46, pp. 53–60(1990).

Tetrahydrofuran has been added to the inert carrier gas which reportedly improves the volatility of "Ba(thd)$_2$"; see S. Matsuno et al, Japanese J. Appl. Phys., Vol. 29, pp. L947–L948 (June, 1990) and Chern et al, Appl. Phys. Lett., Vol. 57, pp. 721–723 (Aug., 1990). The problems associated with this technique include the unknown chemical identity and changing nature of the gas phase species. If a substantial pressure of added ligand is needed then the CVD processing cannot be accomplished at low pressures thereby losing the inherent advantages of operating in this regime; K. K. Schuegraf, "Handbook of Thin Film Deposition Processes and Techniques", Noyes Publication, 1988, Chapter 3. In addition, since oxygen gas is introduced into the system to effect the oxide deposition, there exists a danger of forming an explosive gas mixture within the CVD reactor since the added ligands are typically flammable or combustible.

A recent publication reports on the study of bis(2,2,6,6-tetra-methyl-3,5-heptanedionato)-tris(methanol)barium, monomethanol, [Ba(C$_{11}$H$_{19}$O$_2$)$_2$(C-H$_3$OH)$_3$·CH$_3$OH], and one of its derivatives used as a barium precursor in OMCVD; A. Gleizes et al, C. R. Acad. Sci. Paris, Vol. 312, II, pp. 983–988 (March, 1991).

The foregoing prior art OMCVD precursor compositions (a) are reportedly stable for short time periods, or (b) require the addition of an extra stage to the precursor delivery to achieve additional stability control, or (c) incorporate an excess ligand (e.g. amines/ammonia) which can lead to safety/flammability problems. Such prior art complexes are in contrast to complexes that are in effect composed of non-polymeric discreet "clusters" of barium atoms (i.e. y=2-10) and that are cleanly volatile, undergo no chemical decomposition upon sublimation and require no addition of adduct forming ligand to help in sublimation. Such a compound should be highly suited to CVD processes, especially at low pressures. It is evident from a reading of the number of prior art references in this area that a long heart felt need exists for such a stable, cleanly volatile barium precursor for OMCVD.

SUMMARY OF THE INVENTION

The composition of the present invention is a barium β-diketonate complex represented by the structural formula:

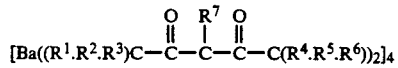

wherein $R^1$, $R^2$, $R^3$, $R^4$, $R^5$, $R^6$, $R^7$ are each independently a $C_1$–$C_6$ group or H, except that each of the two groups of substituents, $R^1$, $R^2$ and $R^3$ and $R^4$, $R^5$ and $R^6$ must have at least two $C_1$ to $C_6$ groups.

The barium complex of the present invention consists of a "cluster" of four barium atoms and eight organic ligands having a semispherical organometallic structure that sublimes cleanly without the need to add additional ligands. Due to the stability and clean evaporation at elevated temperatures of such a complex, it is highly suited for use as a barium source in OMCVD processes. Since it is nonfluorinated, it is especially useful as a reactant with oxygen for the deposition of fluoride free, mixed oxide films containing barium(II); such as YBa$_2$Cu$_3$O$_y$ HTSC ceramic thin films, or BaTiO$_3$ and BaSrTiO$_3$ dielectric and ferroelectric thin films.

BRIEF DESCRIPTION OF THE FIGURES

Further features and advantages of the complex of the present the invention can be obtained by reference to the accompanying drawings, in which:

FIG. 6 is a graph showing the effect of time on the deposition rates of barium carbonate onto a substrate at 650° C. and 2 torr using a preferred embodiment of the present invention;

DETAILED DESCRIPTION OF THE INVENTION

Preferably in the structural formula set forth under the SUMMARY OF THE INVENTION the $R_1$, $R_2$, $R_3$, $R_4$, $R_5$, and $R_6$ are each independently a $C_1$–$C_4$ group and $R_7$ is H.

Still more preferably, the $R_1$, $R_2$, $R_3$, $R_4$, $R_5$, and $R_6$ are each a methyl group and this embodiment can be represented by the structural formula $[Ba]_4[thd]_8$, wherein (thd) is 2,2,6,6-tetramethyl-3,5-heptanedionate anion.

The key aspect of the barium β-diketonate compounds of the present invention is the discovery that they can be synthesized to be cleanly volatile and hence useful in the preparation of fluoride free films of barium compounds by OMCVD. Such compounds are a stable source for OMCVD processes over extended periods of time.

Figure 1:
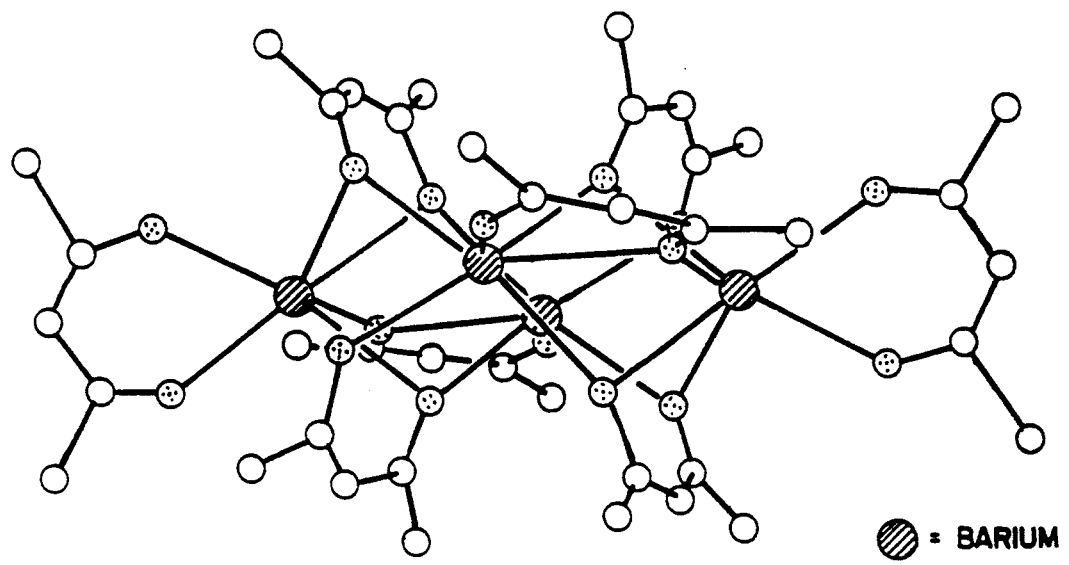
FIG. 1 is a representation of the molecular structure of a preferred embodiment of the barium complex of the present invention (in which methyl groups have been left out for clarity)

The molecular structure of the preferred compound represented by the formula $[Ba]_4[thd]_8$ is shown in FIG. 1 (without the methyl groups). The molecular structure shown in FIG. 1 is in agreement with the structure shown in FIG. 1(a) (without the t-butyl groups) of the paper entitled "Crystalline structure of bis(2,2,6,6-tetramethyl-3,5-heptanedionate) barium", which paper had been submitted by A. Gleizes et al to the C. R. Acad. Sci. Paris to the Editorial Board during the summer of 1991 for review and publication, if approved. Significantly, this structure was obtained from a single crystal of complex that was grown by sublimation, i.e. from the gas phase. Although compounds of the loose description "Ba(thd)₂" have been previously prepared and are commercially available, they are poorly characterized, have undesirably low and variable volatility in addition to undergoing decomposition under sublimation conditions. In a pre-print of paper entitled "Synthesis and Characterization of Alkaline-Earth β-Diketonate Complexes Used as Precursors for Chemical Vapor Deposition of Thin-Film Superconductors" which is scheduled for publication in the fall of 1991 in Inorganic Chem. by S. B. Turnipseed et al, the authors state that they have discovered that the "true" composition of "Ba(thd)₂" is in fact $[Ba]_5[thd]_9(H_2O)_3(OH)$. This statement is supported by an X-ray crystal structure of the complex which is shown in FIG. 2 (without the t-butyl groups).

Figure 2:
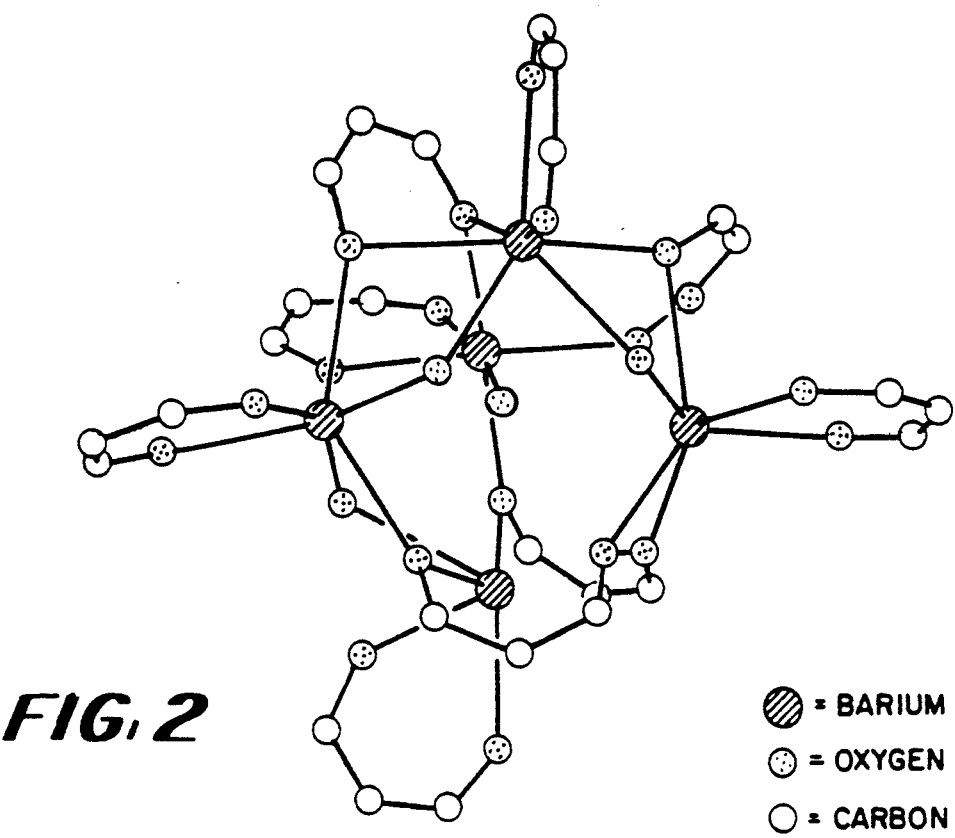
FIG. 2 is a representation of the molecular structure of the barium (thd) complex of the prior art (in which t-butyl groups have been left out for clarity)
Figure 3:
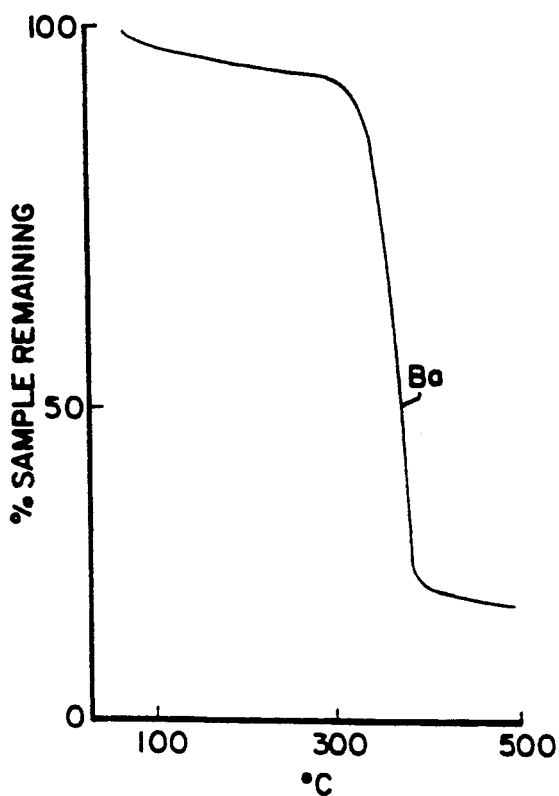
FIG. 3 is a thermogravimetric analysis (TGA) curve of the prior art complex of FIG. 2.
Figure 4:
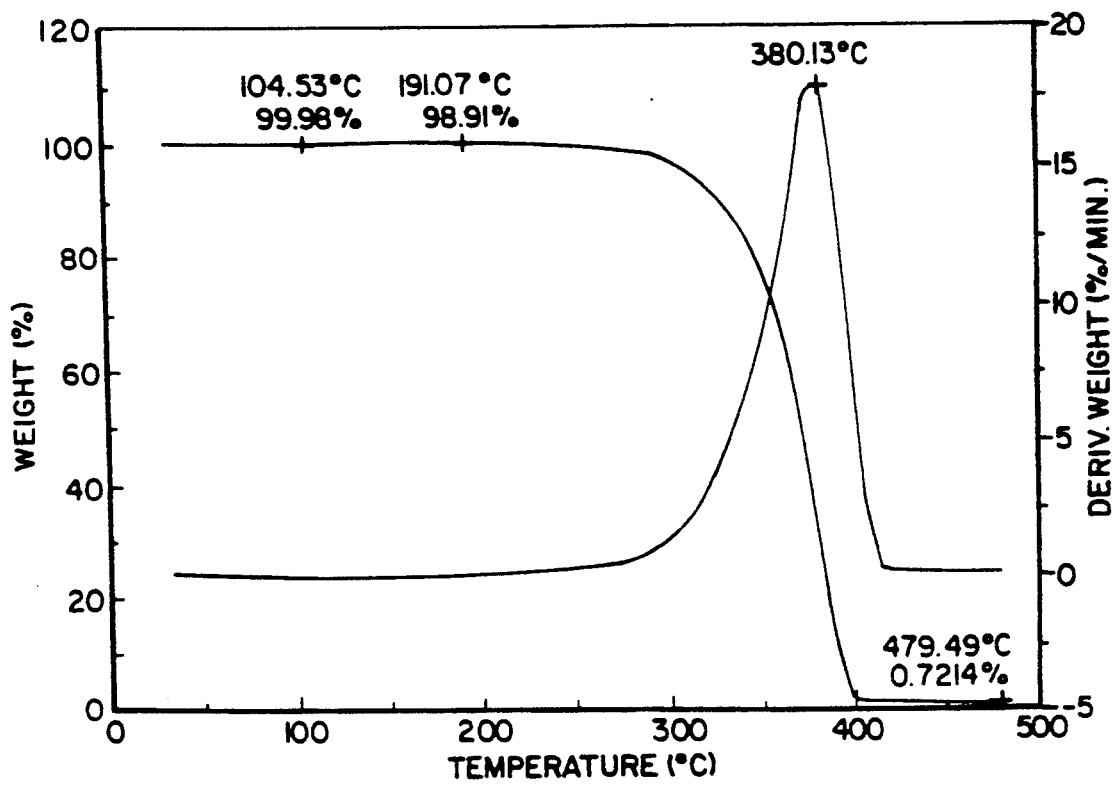
FIG. 4 is a TGA curve of the preferred embodiment of the barium complex of the present invention.

Turnipseed et al arrive at the composition of FIG. 2 by two independent routes, either in the presence of water or ostensibly in its absence. The volatility of this compound is shown by means of a thermogravimetric analysis (TGA) whereby the evaporative weight loss of a sample of complex under a steadily flowing stream of nitrogen is monitored versus time as the temperature of the sample is steadily increased. This results in an approximate 80% weight loss up to approximately 400° C. with 20% involatiles remaining. In contrast to this, under comparable TGA conditions, the complex of the preferred embodiment of the present invention sublimes cleanly with no more than 1% involatile residues thereby indicating it to be more useful in an OMCVD process. The two TGA plots are shown in FIG. 3 and FIG. 4 along with the differences in volatility characteristics shown in Table 1 below.

TABLE 1

| Barium precursor | $[Ba^{+2}]_4[thd^-]_8$ | $[Ba^{+2}]_5[thd^-]_9(OH^-)\cdot 3H_2O$ |
|---|---|---|
| TGA ramp rate | 10° C./min | 20° C./min |
| TGA inert flow rate | 100 ml/min($N_2$) | 80 ml/min(He) |
| Temp. at which effective evaporation of complex ceases | 400° C. | 400° C. |
| Involatile residue remaining | 0.72% | 20% |

Throughout the discussion of the complex of the present invention, the term "OMCVD process" means a process for depositing a uniform, thin film, e.g. 0.01 to 10 microns in thickness, of metal oxide onto a substrate comprising loading a metal complex into a vaporizer or an evaporator comprising a cylindrical tube with gas and thermocouple inlets and outlets at the ends thereof. An inert gas, i.e. argon, nitrogen or helium, is metered by mass flow controllers and passed through the vaporizer, which is heated to a temperature in the range of about 200°–300° C., preferably 220°–250° C., to entrain the vapors of the barium complex. The space velocity of the inert gas through the vaporizer is in the range 0.1 to 10 standard cc/cc/min, and, together with the vaporizer temperature, is adjusted to achieve a dynamically stable and sufficient rate of transport of the barium complex. The entrained barium complex vapor-inert gas mixture is transported to the CVD reactor in heated lines to prevent condensation. The barium complex vapor-inert gas gas feed is combined with an inert gas/oxygen mixture, and optionally with other organometallic complex vapor/inert gas mixtures, and the combined stream is injected into the CVD reactor. Substrates, e.g. sapphire, silicon, strontium titanate or zirconia in the case of HTSC devices, are supported or mounted on a susceptor within the reactor, and are heated by radiation and convection from IR lamps or a furnace, and/or induction from coils surrounding the reactor which coils are powered by a radio frequency (rf) power source. The substrates are maintained at a temperature in the range of 350° to 900° C., preferably 450°–750° C. The lower temperature may be decreased according to the minimum temperature at which the desired product phase can be deposited at an acceptable deposition rate.

Barium carbonate was deposited by OMCVD from the reaction of the preferred complexes of the present invention and oxygen at a reactor pressure of 2 Torr and reactor temperatures in the range 450° to 650° C. At temperatures below 500° C. and a reactor pressure of 2 Torr, the deposition rate of barium carbonate followed an Arrhenius type of relationship with the deposition rate decreasing as the reactor temperature was decreased. The use of microwave plasma or $N_2O$; see Chern et al, Appl. Phys. Lett., Vol. 57, pp. 185–187 (Jan., 1991), ultraviolet light or ozone may be used to facilitate the reaction rate at lower temperatures and/or change the crystallinity of the deposited film.

The CVD reactor pressure can be in the range of about 0.1 to 750 Torr, preferably 1 to 100 Torr, still more preferably 2 to 70 Torr. In one embodiment, the complex is used in the absence of an inert carrier gas, in which case the reactor pressure is closely related to that of the precursor vapor pressure, i.e. in the range of about 0.01 to 1 Torr. In the examples below, it is shown that the tetrameric complex of the present invention which is described above is very effective as a precursor for the OMCVD deposition of thin films containing barium compounds.

EXAMPLES

Experimental

In the following examples, unless otherwise noted, all parts and percentages are by weight.

2,2,6,6-tetramethyl-3,5-heptanedione was purchased from Aldrich Chemical Co. (940 W. St. Paul Avenue, Milwaukee, Wis. 53233). Barium hydride was purchased from Cerac (407 N. 13th Street, Milwaukee, Wis. 53233). The tetrahydrofuran (THF) solvent used in the experiments was dried by distillation from sodium benzophenone under an atmosphere of nitrogen prior to use.

Synthesis of $[Ba]_4[thd]_8$

The following description represents a generic synthesis of a preferred embodiment of the present invention. 2,2,6,6-tetramethyl-3,5-heptanedione (0.5 moles) was slowly added to barium hydride (0.25 moles) as a stirred slurry in 300 ml of THF under a vented atmosphere of $N_2$. Evolution of $H_2$ was observed and when the bubbling had largely subsided, the reaction mixture was gently warmed to an overnight reflux. After the mixture had been cooled, any major solid impurities remaining were filtered from solution. THF was stripped from the clear filtrate by the application of vacuum initially at room temperature and then by slowly heating the solution to a maximum of 150° C. until no further volatiles were observed to be emerging from the crude product. After stripping, the crude product was sublimed one or more consecutive times at 50 m Torr and 230°–250° C. The number of times the particular sample was sublimed in the examples below is included in the batch number, i.e. batch #BAM 12390-1-Subl of Example 1 was sublimed once. If during the sublimation, oils were observed to be liberated from the subliming product, they were isolated as a white solid. The average yield obtained during each synthesis was 80%. Elemental microanalysis:

Found: C 50.31%, H 7.77%, Ba 29.01%
Calculated: C 52.44%, H 7.54%, Ba 27.26%

Additional elemental microanalyses were conducted at Oneida Research Services on four separate samples (sample numbers #1991, #6591, #52291, and #51591) of $[Ba]_4[thd]_8$, which produced %C 52.16 %H 7.74, %C 52.42 %H 7.76, %C 52.49 %H 7.70, and %C 52.28 %H 7.71, respectively. These values are in good agreement with the theoretical values. The barium concentration was determined by ICPAA (inductively coupled plasma atomic absorption) analysis, and found to be 28.0/0.2% Ba (at the 95% confidence interval with three replicates), in close agreement with the theoretical value.

EXAMPLES OF OMCVD

Example 1

Figure 5:
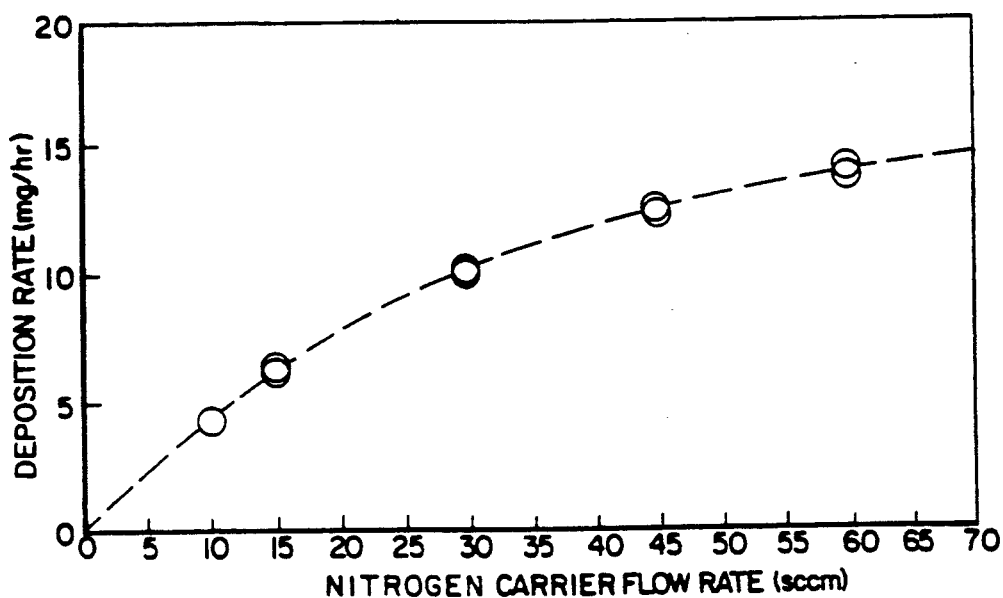
FIG. 5 is a graph of the deposition rates of barium carbonate onto a substrate at 650° C. versus the flow rate of the nitrogen carrier gas that has come into contact with the complex of a preferred embodiment of the present invention.

A ~10 g charge of $[Ba]_4[thd]_8$ prepared in accordance with the procedures set forth above (batch #BAM 12390-1-Subl) was loaded into a stainless steel bubbler comprising a source for the charge, with an internal volume of approximately 55 cm³ and fitted within a ⅜ inch I.D. metal feed tube capped by a ¼ inch 10 micron pore size sparger,. The source was heated by an external heater to a temperature of 220° C., i.e. above the melting point of the complex which was determined by DSC to be 215° C. The bubbler was allowed to reach thermal equilibrium prior to any OMCVD studies. In a series of four runs, nitrogen carrier gas was bubbled through the complex within the source at flow rates of 15, 30, 45, and 60 sccm to transfer the complex to the OMCVD reactor. This feed gas was mixed with 40 sccm of oxygen and a balance of nitrogen gas added to provide a total flow rate of 100 sccm prior to entering the cold wall OMCVD reactor. The reactants were passed over a heated calcia (~5 wt. %) stabilized zirconia (CSZ) substrate discs (3 mm thick and 20 mm diameter obtained from Johnson Matthey) which were hung vertically in the OMCVD reactor at 650° C., a total reactor pressure of 2 Torr and an oxygen partial pressure of 0.8 Torr. Deposition rates of barium carbonate at each carrier gas flow rate were measured in-situ by suspending the sample from a microbalance. Each run was of approximately 30 minutes duration. Repeat experiments were performed the following day, with the addition of a run at 10 sccm carrier gas through the source. Good agreement between the two days experiments were observed as shown in FIG. 5. Additionally, on the first day an extended run of 90 mins duration was conducted at a nitrogen carrier gas flow rate of 60 sccm. After an initial stabilization period of 15 minutes, the deposition rate of barium carbonate was found to be constant.

Example 1 shows the stability and reproducibility of the $[Ba]_4[thd]_8$ compound when used as an organometallic Ba precursor. The formation of $BaCO_3$ by reaction with $O_2$ is as expected from the relative values of the free energy of formation of $BaCO_3$ and BaO under the conditions of the experiments, i.e. at 650° C. BaO would be formed at higher temperatures at which $BaCO_3$ is unstable, e.g. at >850° C. X-ray diffraction analysis of sample Example 1 confirmed that highly crystalline $BaCO_3$ was deposited. Scanning electron microscopy studies along a fractured cross section of sample of Example 1 revealed a columnar morphology.

Example 2

A 20 g charge (batch #BAM 1991-3-Subl) of $[Ba]_4[thd]_8$ prepared in accordance with the procedures set forth above was loaded into same stainless steel bubbler and barium carbonate was OMCVD deposited on CSZ discs in the same manner as described under Example 1 above. In a series of runs over a period of 2 months, nitrogen carrier gas was bubbled through the complex within the source at flow rates of 7 to 30 sccm to transfer the complex to the OMCVD reactor.

In total, the source remained in the OMCVD reactor for a three month period, throughout which the $[Ba]_4[thd]_8$ was maintained under vacuum or in an atmosphere of nitrogen. During its use in the OMCVD reactor, the original 20 g load (batch BAM #1991-3-Subl)

was subjected to 13 heat cycles inside the stainless steel bubbler, between room temperature and the operating temperature of 220° C. (with a high temperature hold of 3-6 hours in each cycle).

Figure 8:
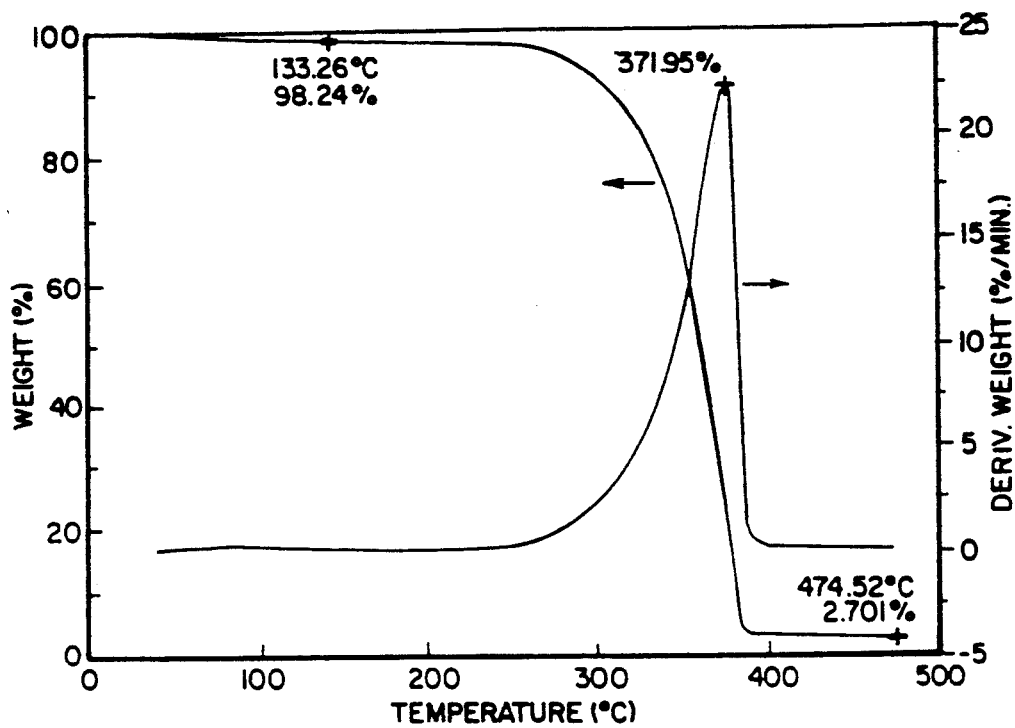
FIGS. 8 and 9 are TGA curves of samples of a preferred embodiment of the present invention after aging studies.
Figure 9:
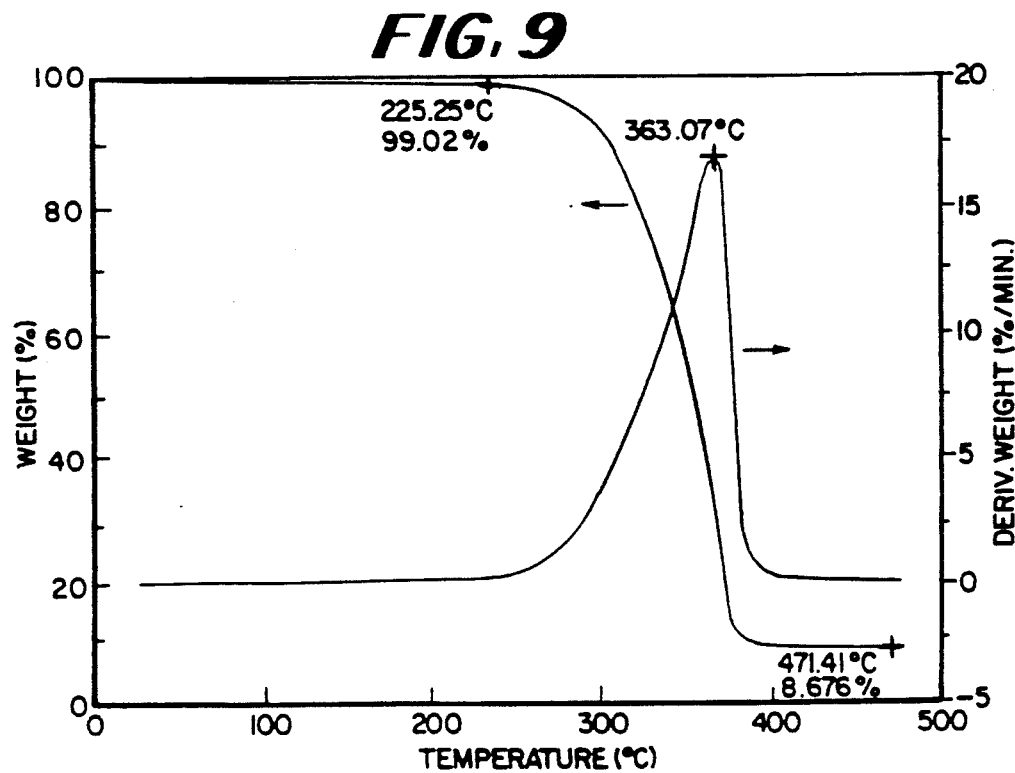

Following the three month period the bubbler was emptied and found to contain 6.43 g of material, which represents 32% of the original $[Ba]_4[thd]_8$ charge. The material was mainly a powder, light brown in color, with ~15 vol % of the sample made up by dark brown agglomerates (the original charge of the complex was white/light yellow powder). The sample was analyzed by TGA, separately as the light brown powder and the dark brown agglomerates. The light brown powder produced a smooth TGA curve as shown in FIG. 8. This curve is typical of $[Ba]_4[thd]_8$ as shown in FIG. 4, with a high temperature residue of 2.7% and a maximum derivative peak at 372° C. The darker colored agglomerates gave a smooth TGA curve as shown in FIG. 9, however with a larger high temperature residue of 8.7% and a derivative maximum at 363° C. Hence, the TGA analyses confirm the long term stability of the $[Ba]_4[thd]_8$ precursor for OMCVD applications when operated in the above manner.

OMCVD data presented in FIG. 6 represents the performance of the source over its first month use, with the legends referring to the day the precursor was used dated from when the source was loaded with the 20 g $[Ba]_4[thd]_8$ charge. The OMCVD studies of the sample of Example 2 indicated that the deposition rates slowly declined over the initial one month period, to achieve similar deposition rates to those obtained for the smaller 10 g charge of $[Ba]_4[thd]_8$ employed in Example 1. It is thought that this may be due to the variation in bed depth of the material inside the bubbler with use. Following the initial rate decline, the source continued to behave in a reproducible fashion during the subsequent OMCVD runs over the second month period.

Figure 7:
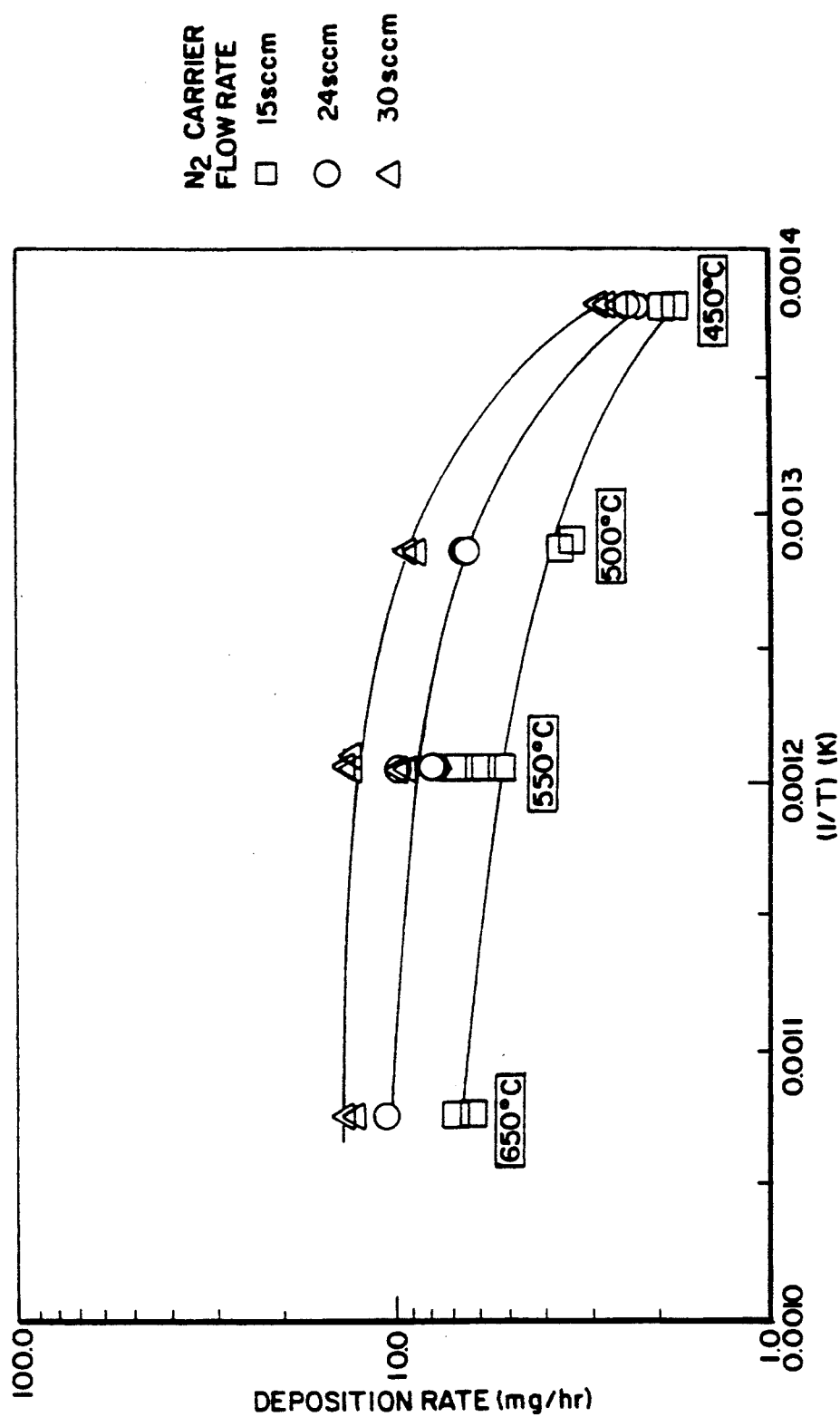
FIG. 7 is a graph showing the effect of substrate temperature on the deposition rates of barium carbonate onto substrates ranging in temperature from 450°–650° C. using a preferred embodiment of the present invention.

For example, the deposition rates using the $[Ba]_4[thd]_8$ source of Example 2 were sufficiently stable over an extended period of several days, which allowed a study of the effect of substrate temperature on the deposition rate over the temperature range 450°-650° C. as shown in FIG. 7 (data measured on day 22, day 23, day 24, day 25, day 44, and day 45). The temperature dependence of deposition rate indicated gas phase mass transfer resistance to be rate controlling for $BaCO_3$ deposition at substrate temperatures above ~500° C.

Example 3

Figure 10:
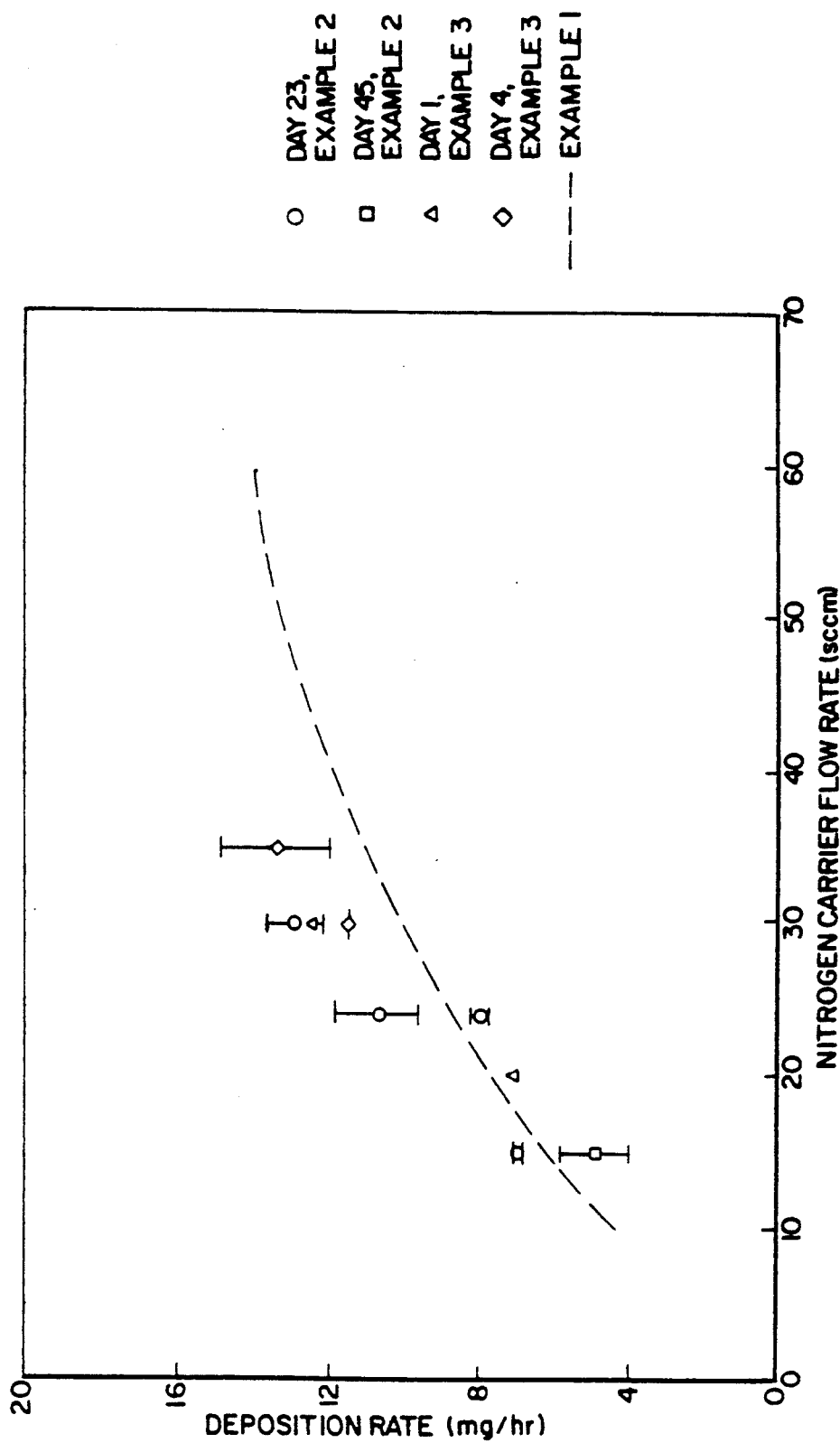
FIG. 10 is a graph showing the effect of time on the deposition rates of barium carbonate onto a substrate at 550° C. and 2 torr using a preferred embodiment of the present invention.

A 15 g charge (batch #BAM 4991A-2-Subl, Example 3) of $[Ba]_4[thd]_8$ prepared in accordance with the procedures set forth above was loaded into same stainless steel bubbler as in Example 1, and barium carbonate was OMCVD deposited at 550° C. and 2 Torr reactor pressure on CSZ discs in the same manner as described under Example 1 above. OMCVD data obtained at 550° C. for the 15 g sample of Example 3 (on day 1 and day 4 with respect to the date which the source was loaded with the 15 g $[Ba_4[thd]_8$ charge) are shown in FIG. 10. Good agreement was obtained between the data of each of Example 1, Example 2 (on day 23 and day 45), and Example 3, confirming the excellent long term stability and control of precursor transport rate achieveable with $[Ba]_4[thd]_8$ provided the bubbler is suitably charged to minimize the effects of entrainment and bed depth variation in the source.

THERMAL ANALYSIS STUDIES

Examples 4, 5 and 6

Two samples of $[Ba]_4[thd]_8$ prepared in accordance with the procedures set forth above (batch #BAM 4991A-2-Subl) were submitted for TGA and DSC. Following synthesis, the samples had been purified with two vacuum sublimations and samples were placed into glass vials with septum screw tops and the vials were stored inside a nitrogen glove box for a period in excess of a month. One of the samples, Example 4, was studied immediately after this period by TGA and DSC, and the remainder of the sample, the aged sample (Example 5), was left exposed to air for a period of 10 days. This aged sample was rerun after 10 days, together with the second sample, Example 6, which had been left sealed in the open laboratory.

Figure 11:
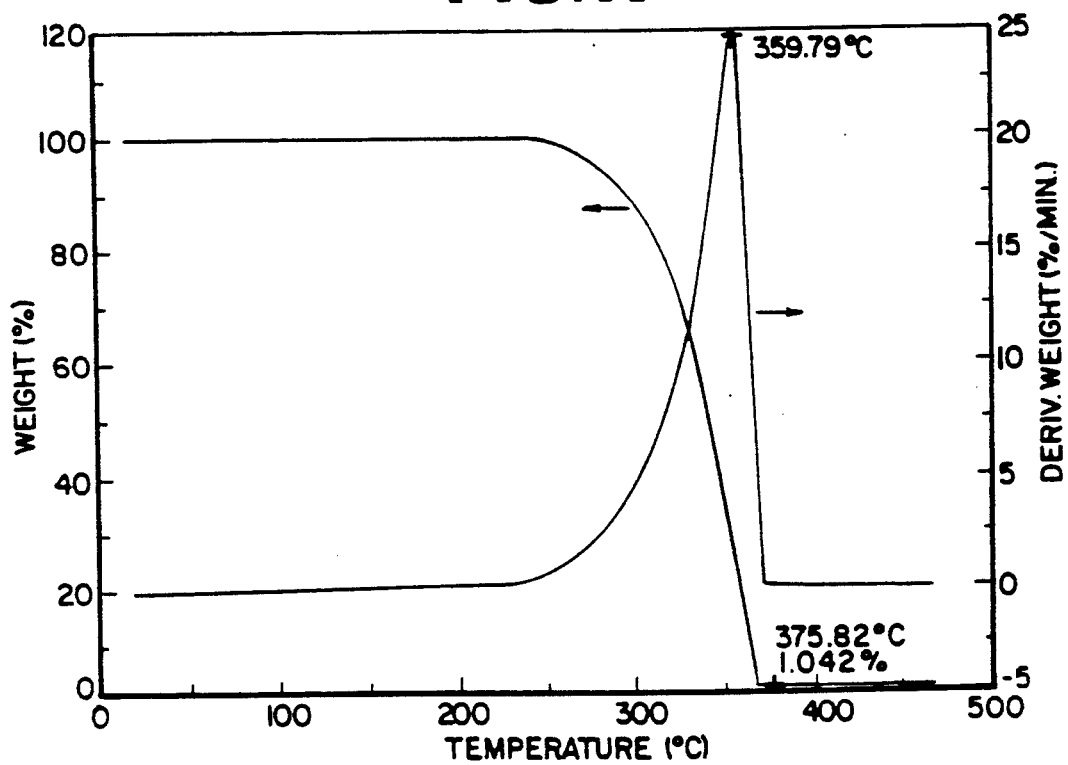
FIGS. 11, 12 and 13 are TGA curves showing the effect of moisture on samples of a preferred embodiment of the present invention.
Figure 12:
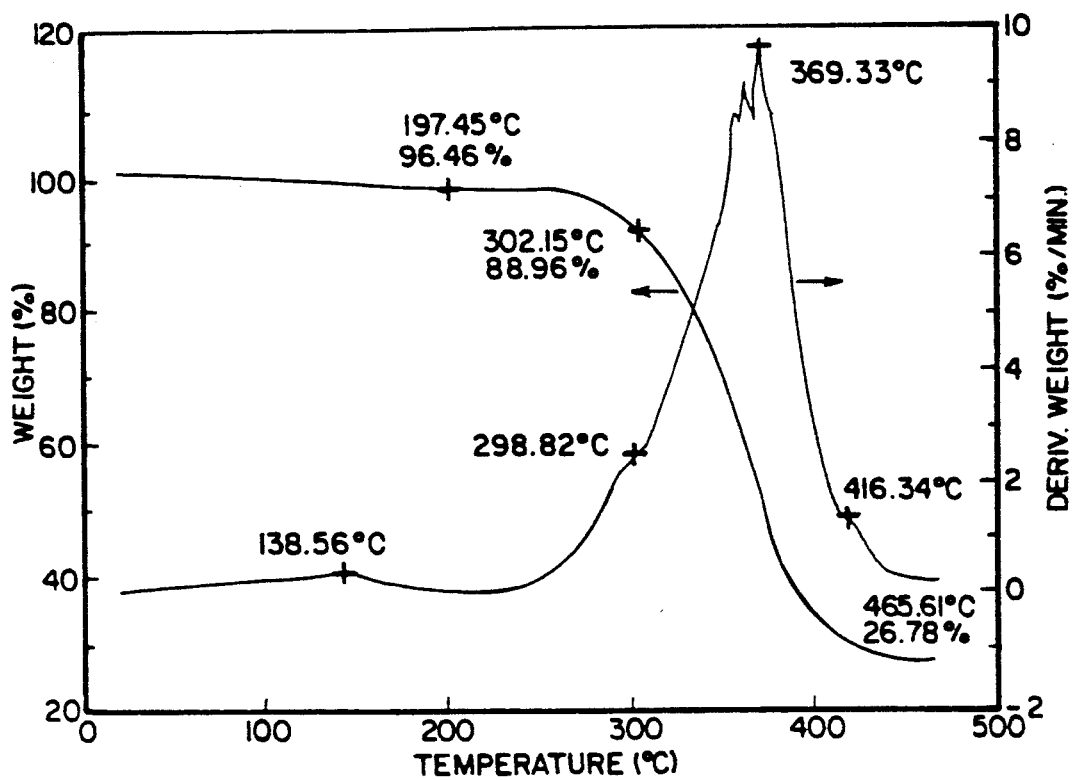
Figure 13:
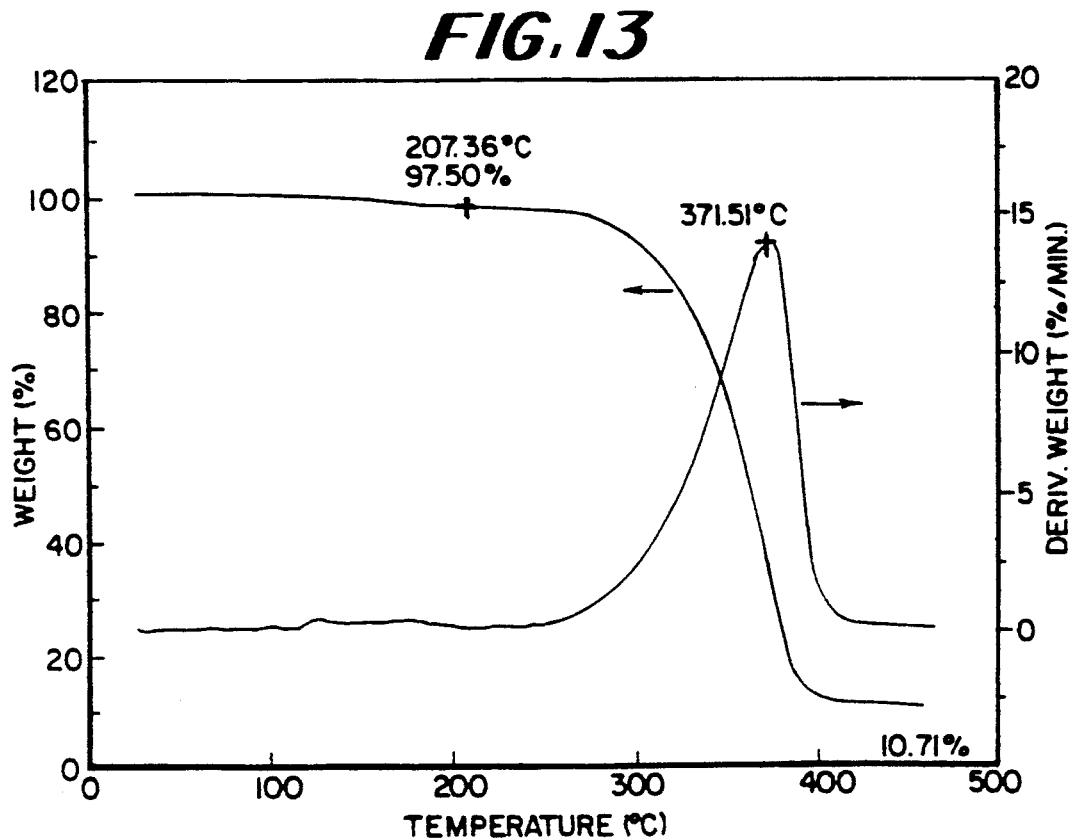

The TGA of the Example 4 revealed a smooth curve showing a maximum weight loss rate at 360° C. and a high temperature residue of 1%; see FIG. 11. The clean vaporization, without decomposition, of the sample reflects the attractiveness of preferred complex of the present invention as a Ba precursor for OMCVD applications. In contrast, the Example 5 sample purposefully aged in air for 10 days possessed a more complex TGA trace as shown in FIG. 12, with several peaks in the weight loss derivative, and a 27% residue, which is indicative of degradation of the complex. Significantly, the Example 6 sample produced an 11% high temperature residue, and a derivative peak centered at 372° C.; see FIG. 13. The degradation of the Example 6 sample was interpreted as being due to air entering the vial through the septum seal, during storage in the open laboratory.

INFRA-RED SPECTROSCOPY STUDIES

Examples 7 and 8

Samples of $[Ba]_4[thd]_8$ (Example 7), $[Ba]_4[thd]_8$ exposed to air (Example 8), and a commercial sample of $Ba(thd)_2$ supplied by Strem Chemicals, Inc, were analyzed by infra-red spectroscopy to investigate whether the samples were hydrated (the 3500-3000 $cm^{-1}$ region contains the O-H stretch band, and is therefore indicative of water). The commercial $Ba(thd)_2$ showed pronounced amounts of hydration, as did the $[Ba]_4[thd]_8$ exposed to air. The latter displays the ease with which $[Ba]_4[thd]_8$ will hydrate when exposed to atmospheric moisture. In contrast, $[Ba]_4[thd]_8$ stored under nitrogen in a glove box possessed a near featureless spectrum over the 3500-3000 $cm^{-1}$ range, confirming the absence of water in the sample.

Example 9

Samples of $[Ba]_4[thd]_8$ (Example 3) exposed to air to contact the sample with moisture (Example 9) and a commercial sample of $Ba(thd)_2$ hydrate (lot #1104-P) supplied by Strem Chemicals, Inc, were analyzed by TGA. The TGA curves for both the Example 9 sample and the commercial sample run in nitrogen showed considerable high temperature residues of 18.1 and 30.7 Wt. %, respectively, with multiple peaks in the derivative weight loss curves indicating decomposition of each of the barium precursors. The two samples were subjected to each of the two procedures set forth in the A. D. Berry et al reference discussed under the Background of the Invention section above.

In the first procedure, the precursors were heated in accordance with the method of Berry et al under a stream of nitrogen for about 30 minutes. Specifically, both the Example 9 and commercial precursors were conditioned on the TGA instrument in flowing nitrogen at 130° C. for an hour. The TGA analyses of the two samples indicated that the high temperature residues were respectively 17.0 and 30.2 wt. % with multiple peaks in the derivative weight loss curves. This demonstrated that the first procedure of the Berry et al reference did not improve the vaporization of either precursor.

In the second method of the Berry et al reference, samples of the two precursors were heated at 130° C. in vacuo. Following the vacuum conditioning, the TGA analyses of the two samples showed high temperature residues of 5.6 and 29.1 wt. % for the Example 9 and commercial samples, respectively, again with significant multiple peaks in the derivative weight loss curve. The hydrated Example 9 precursor did appear to vaporize with less degradation following the vacuum pretreatment. This result of 5.6 wt. % residue and pronounced multiple peaks should be compared to the residue of 1 wt. % and the smooth TGA curve as shown in FIG. 11 for the Example 4 sample. Therefore, while this prior art conditioning method does appear to effect the vaporization properties of the previously hydrated precursors of the present invention, it does not reproduce the properties of virgin $[Ba]_4[thd]_8$.

Example 10

$[Ba]_4[thd]_8$ is fed into an OMCVD reactor in a nitrogen carrier gas according to the procedure described in Example 1 above. The $[Ba]_4[thd]_8$-containing feed gas is mixed with $O_2$ and passed over a MgO substrate maintained at 875° C. and a reactor pressure of 2 Torr to deposit a thin film of BaO in place of $BaCO_3$ onto the substrate.

Example 11

$[Ba]_4[thd]_8$ is fed into an OMCVD reactor in a nitrogen carrier gas according to the procedure described in Example 1 above. The $[Ba]_4[thd]_8$-containing feed gas is mixed with a feed of titanium tetraisopropoxide (Ti-$(OC_3H_7)_4$) transported in a nitrogen carrier gas. The latter feed gas is generated in a stainless steel bubbler of the same type as that used to generate the $[Ba]_4[thd]_8$ feed except that the temperature of the bubbler is maintained at 30° C. instead of the 220° C. temperature of the bubbler for the barium precursor. The flow rates of the two precursor feed streams in the presence of oxygen are adjusted to achieve the correct stoichiometry for a deposition of thin film of $BaTiO_3$ onto a substrate of $SrTiO_3$ at 600° C. and 2 Torr.

Example 12

$[Ba]_4[thd]_8$, $Y[thd]_3$ and $Cu[thd]_2$ are co-fed into the OMCVD reactor in a nitrogen carrier gas according to the procedure described in Example 1 above. The $[Ba]_4[thd]_8$ stainless steel bubbler is maintained at 220° C., the $Y[thd]_3$ bubbler is maintained at 130° C., and the $Cu[thd]_2$ bubbler is maintained at 120° C. The precursor gas streams are mixed at the entrance to the OMCVD reactor with an oxygen stream. The flow rates of the three precursor feed streams in the presence of oxygen are adjusted to achieve the correct stoichiometry for a deposition of a thin film of $YBa_2Cu_3O_{3-x}$ onto a substrate of $SrTiO_3$ at 850° C. and 2 Torr.

Examples 13 and 14

Other homologs of the complex of the present invention can be synthesized using the same procedures used to prepare $[Ba]_4[thd]_8$ as set forth above.

In place of 2,2,6,6-tetramethyl-3,5-heptanedione, a β-diketone is synthesized via a standard Claisen condensation (The Merck Index, Merck & Co., Inc., page 1153 (1968)) by the following reaction:

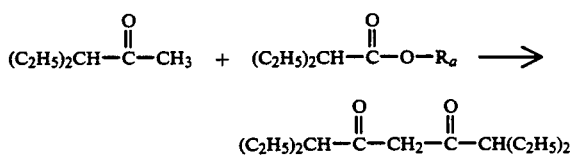

Where $R_a$ is a $C_1$-$C_6$ alkyl group.

The reaction of barium hydride with the β-ketone from the above reaction yields the Example 13 complex having the following structural formula:

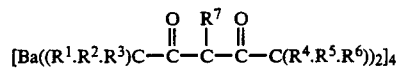

wherein $R^1$, $R^2$, $R^4$ and $R^5$ are each independently an ethyl group and $R^3$, $R^6$ and $R^7$ are each independently H.

In a similar manner, another β-diketone can be synthesized by the following reaction:

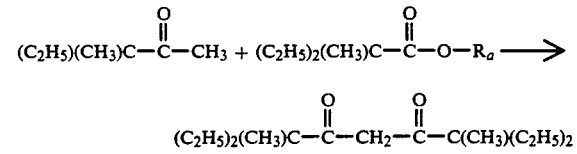

Where $R_a$ is a $C_1$-$C_6$ alkyl group.

The reaction of barium hydride with the β-ketone from the above reaction yields the Example 14 complex having the following structural formula:

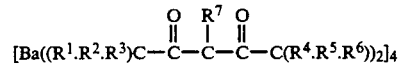

wherein $R^1$, $R^2$, $R^4$ and $R^5$ are each independently an ethyl group, $R^3$ and $R^6$ are each independently a methyl group and $R^7$ is H.

CONCLUSIONS

The complex of the present invention has been shown to be cleanly volatile, to undergo no chemical decomposition upon sublimation, to require no addition of adduct forming ligand to help in sublimation, and to be a stable OMCVD precursor over relatively long time periods, i.e. a period in excess of three months.

Various modifications of the invention in addition to those shown and described herein will become apparent to those skilled in the art from the foregoing description and examples. Such modifications are intended to fall within the scope of the appended claims.

What is claimed is:

1. A volatile organometallic complex represented by the structural formula:

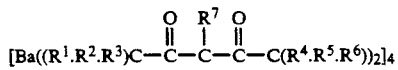

wherein $R^1$, $R^2$, $R^3$, $R^4$, $R^5$, $R^6$, $R^7$ are each independently a $C_1$-$C_6$ group or H, except that each of the two groups of substituents $R^1$, $R^2$ and $R^3$ and $R^4$, $R^5$ and $R^6$ must have at least two $C_1$ to $C_6$ groups.

2. The complex in accordance with claim 1 wherein $R^1$, $R^2$, $R^3$, $R^4$, $R^5$, and $R^6$ are each independently a $C_1$-$C_4$ group and $R^7$ is H.

3. The complex in accordance with claim 2 wherein $R^1$, $R^2$, $R^3$, $R^4$, $R^5$, and $R^6$ are each a methyl group.

* * * * *